US00PP24947P3

(12) United States Plant Patent
Jenkin et al.

(10) Patent No.: US PP24,947 P3
(45) Date of Patent: Oct. 7, 2014

(54) TANGOR TREE NAMED 'RHM'

(50) Latin Name: ***Citrus reticulata*×*Citrus sinensis***
Varietal Denomination: RHM

(75) Inventors: Allen Ward Jenkin, Mundubbera (AU); Susan Ruth Jenkin, Mundubbera (AU)

(73) Assignee: Royal Honey Pty Ltd ATF Royal Honey IP Trust, Mundubbera, Queensland (AU)

( * ) Notice: Subject to any disclaimer, the term of this patent is extended or adjusted under 35 U.S.C. 154(b) by 98 days.

(21) Appl. No.: 13/385,765

(22) Filed: Mar. 5, 2012

(65) Prior Publication Data

US 2013/0232650 P1 Sep. 5, 2013

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

U.S. PATENT DOCUMENTS

PP17,863 P3 * 7/2007 Roose et al. ..... Plt./201
PP22,649 P3 * 4/2012 Roose et al. ..... Plt./201

OTHER PUBLICATIONS

UPOV PLUTO 201303 AU Citation for 'RHM' Mar. 24, 2006.*

* cited by examiner

*Primary Examiner* — Wendy C Haas
(74) *Attorney, Agent, or Firm* — Michelle Bos

(57) ABSTRACT

'RHM' is a new and distinct tangor tree notable for its high quality fruit with rich mandarin flavor.

3 Drawing Sheets

Genus and species: *Citrus reticulata*×*Citrus sinensis*.
Variety denomination: 'RHM'.

BACKGROUND AND SUMMARY OF THE VARIETY

The new tangor variety 'RHM' originated as a chance seedling discovered in 2001 in a cultivated planting at Eidsvold, Queensland, Australia. It is believed to be the progeny of female parent 'Ellendale' tangor (not patented) and male parent 'Murcott' tangor (not patented). The seedling was asexually reproduced by grafting in 2001 at Eidsvold, Queensland, Australia and was observed to determine whether the desired characteristics of the chance seedling would carry through to asexually propagated progeny. It has been found that the distinguishing characteristics of the tree and fruit of the newly discovered variety are reproduced through asexual propagation and have remained stable through successive generations.

'RHM' is a new and distinct tangor tree notable for its high quality fruit with rich mandarin flavor. 'RHM' has been compared to 'Empress A' mandarin (not patented), a similar variety, and is distinguished by its fruit, with lower acid levels, a unique taste profile, more intense red/orange skin and flesh color, and distinct maturity times. Trees of 'RHM' are distinguished from 'Empress A' by their increased vigor and more upright growth habit.

BRIEF DESCRIPTION OF THE PHOTOGRAPHS

Figure 1:
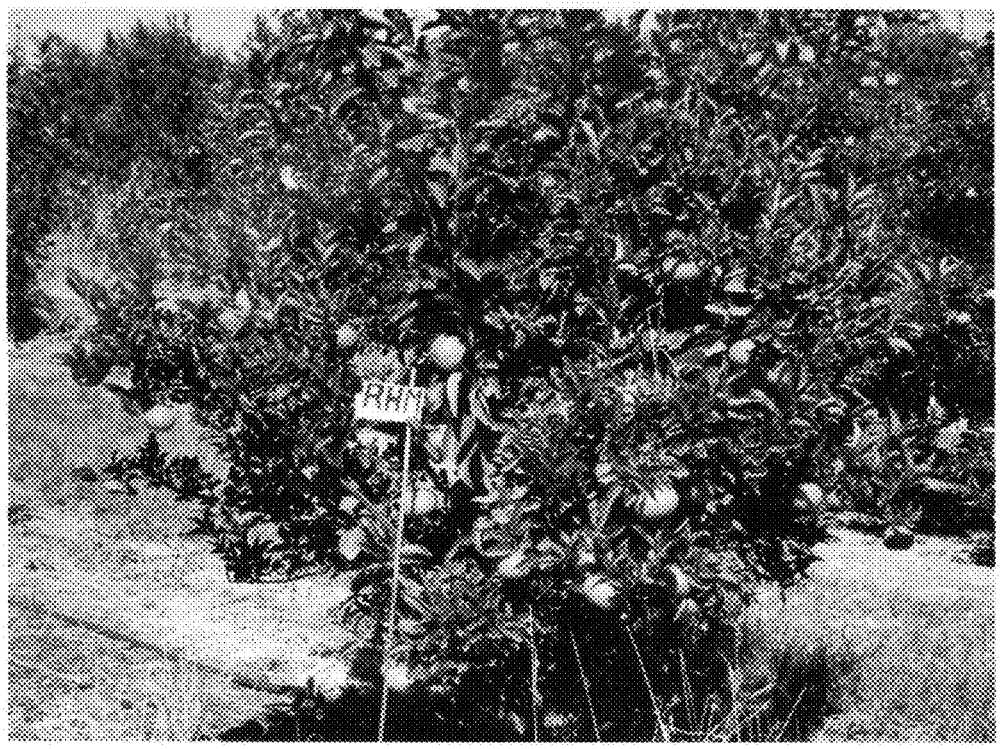
FIG. 1 shows the tree of 'RHM' tangor.
Figure 2:
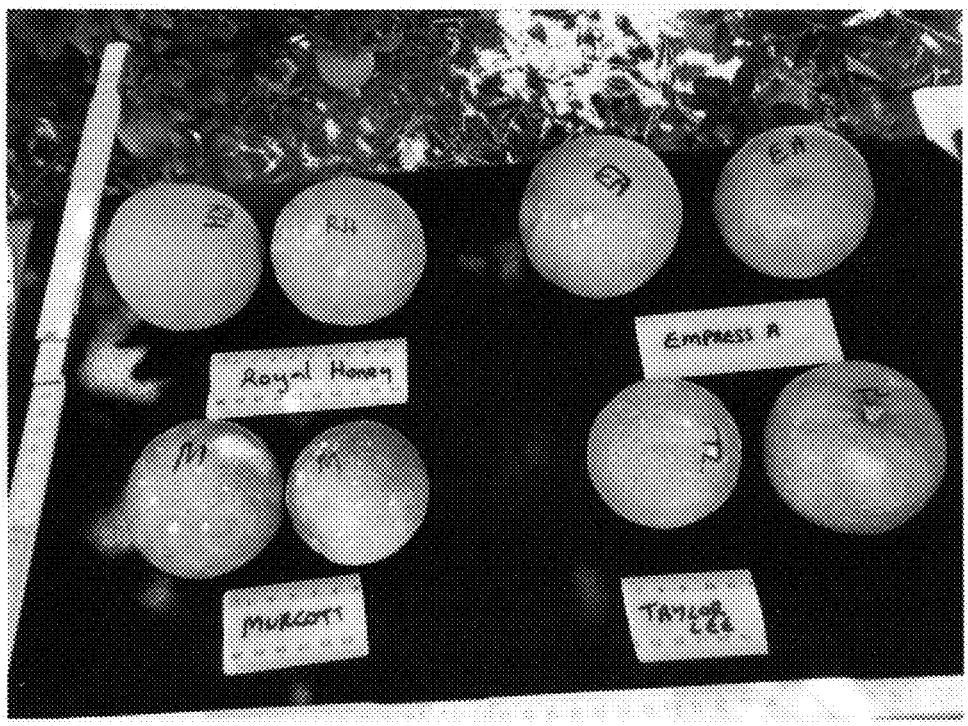
FIG. 2 shows fruit of 'RHM' (labeled "RH" and "Royal Honey") as compared to 'Empress A', 'Murcott' and 'Taylor Lee'; and, FIG. 3 shows the skin, flesh and seeds of 'RHM' (labeled "RH" and "Royal Honey") as compared to 'Empress A'.
Figure 3:
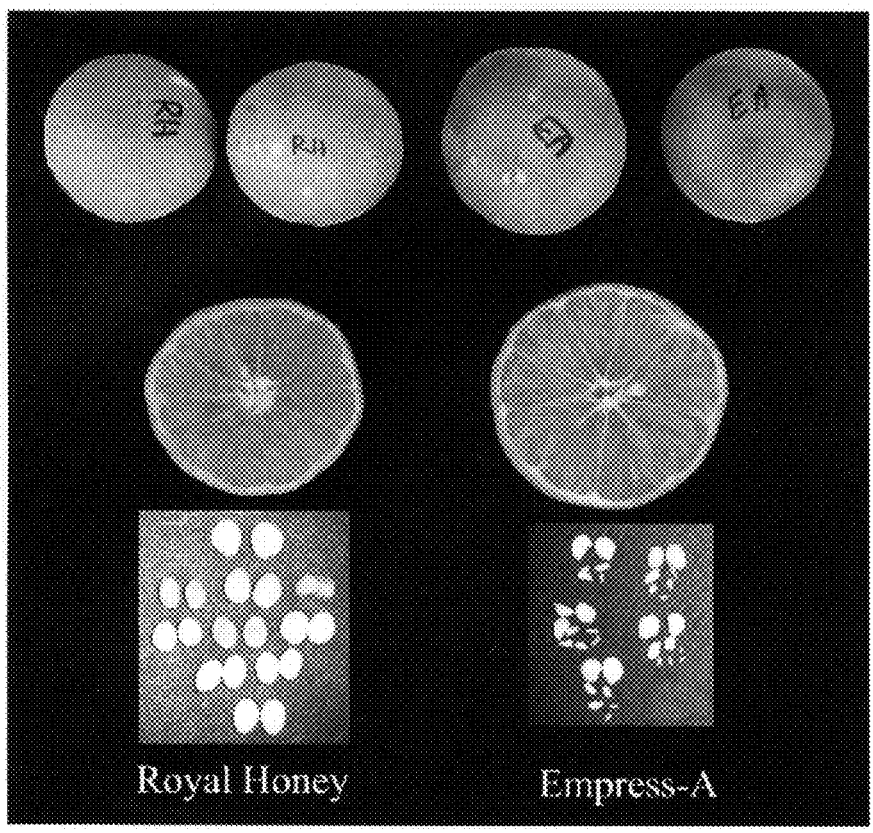

The colors of these illustrations may vary with lighting conditions. Color characteristics of this new variety should therefore be determined with reference to the observations described herein, rather than from these illustrations alone.

DETAILED BOTANICAL DESCRIPTION

The following detailed botanical description is based on observations of trees and fruit of 'RHM', planted in 2006 and grown on 'Troyer Citrange' rootstock (not patented). Observations were recorded and photographs taken during the 2006 to 2011 growing seasons at Eidsvold, Queensland, Australia. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (2007).

Tree:

*Vigor*.—Vigorous; more vigorous than 'Nova' mandarin (not patented), less vigorous than 'OR4' mandarin (not patented).

*Density of canopy*.—Open.

*Habit*.—Upright.

*Height*.—1.4 to 3.0 m.

*Spread*.—1.5 to 2.0 m.

*Trunk diameter* (*at* 30 *cm above the graft*).—10 cm.

*Bark texture*.—Smooth to medium.

*Bark color*.—Grey Orange 164D, Grey Green N144A, Grey Purple N187C.
*Trunk lenticels*.—Smooth, weak phellogen expression; elliptical shape.
*Thorns*.—Few present on juvenile growth; very few to none present on mature tree.
*Winter hardiness*.—Good, similar to 'Ellendale'; exposure to freezing temperatures for extended periods will result in damage to foliage and fruit.
*Drought tolerance*.—Good.

Branch (fruiting branches located at around 1 m above the graft union):
*Length*.—50 cm.
*Diameter*.—1.6 cm.
*Crotch angle*.—15° to 45°.
*Bark color*.—Young wood green 143A; mature branches greyed green. 193A, becoming greyed purple N187D as lignification increases.
*Bark texture*.—Smooth to medium.
*Current year shoot length*.—45 cm.
*Current year shoot color*.—Green 143A.

Flowers:
*Bud length*.—8 to 10 mm.
*Bud diameter*.—5 to 7 mm.
*Bud color*.—Cream white 162C.
*Bud surface texture*.—Smooth.
*Pedicel length*.—6 mm.
*Pedicel diameter*.—1 mm.
*Pedicel color*.—Cream white 162C.
*Sepal length*.—2.6 mm.
*Sepal width*.—2.3 mm.
*Sepal shape*.—Arch.
*Sepal color*.—Yellow 8B.
*Sepal surface texture*.—Upper and lower surfaces smooth.
*Petal length*.—11 mm.
*Petal width*.—56 mm.
*Petal color*.—Upper surface — Green 142D.
*Petal color*.—Lower surface — White NN155D.
*Petal surface texture*.—Upper and lower surfaces smooth.
*Pistil*.—Quantity per flower — 1.
*Pistil length*.—9.6 mm.
*Stigma length*.—2.4 mm.
*Stigma color*.—Yellow-green 151C.
*Style length*.—7 mm.
*Style color*.—Yellow-green 144D.
*Ovary length*.—1.8 mm.
*Ovary diameter*.—3 mm.
*Ovary color*.—Green 141A.
*Anther length*.—8.5 mm.
*Anther color*.—Yellow-green 145D.

Leaves:
*Length*.—Medium to long.
*Width*.—Medium to broad.
*Length/width ratio*.—Medium.
*Leaf shape*.—Ovate.
*Apex shape*.—Acute.
*Base shape*.—Obtuse.
*Color of upper surface*.—Green 143A.
*Color of lower surface*.—Green N144C.
*Leaf texture*.—Smooth to Medium.
*Venation*.—Pinnate.
*Vein color*.—Green 143A.
*Petiole length*.—Medium.
*Petiole diameter*.—2 mm.
*Petiole color*.—Green 143A.
*Wings*.—Present.
*Wing width*.—3.5 mm.

Fruit:
*Fruit height*.—Medium to large, about 58 mm.
*Fruit width*.—Medium to large, about 80 mm.
*Weight*.—133 to 260 grams.
*General shape in profile*.—Slightly rounded.
*Navel*.—Occasionally present.
*Rind color*.—Orange Yellow 25B.
*Oil glands per cm*$^2$.—9.
*Oil gland diameter*.—0.93 mm.
*Rind thickness*.—2.31 mm.
*Ease of peeling*.—Easy to peel (good).
*Rind texture*.—Smooth to medium.
*Albedo thickness*.—1.47 mm.
*Albedo color*.—Cream white NN155A.
*Quantity of fruit segments per fruit*.—11.
*Toughness of segment membrane*.—Moderate to weak.
*Juice sac length*.—13.8 mm.
*Juice sac shape*.—Elongated.
*Juice sac length to width ratio*.—6:1.
*Juice sac color*.—Orange yellow 23A.
*Juice soluble solids* (° *Brix*).—17.2 to 22.2.
*Relative harvest maturity*.—Mid-season.
*Harvest window* (*date range*).—In Queensland, Australia May to June.
*Seeds*.—Present, but seedless if not cross pollinated.
*Seed length*.—11.46 mm to 13.16 mm.
*Seed diameter*.—8.8 mm.
*Seed color*.—Grey white 157A.
*Quantity of seeds per fruit*.—1 to 10.
*Stem length*.—10 mm.
*Stem diameter*.—2.6 mm.
*Stem color*.—Green 143A.

Harvest yield: 40 to 50 tons per hectare on mature trees.
Market use: Domestic and export markets.
Keeping quality: Good.
Shipping quality: Good.

The invention claimed is:

1. A new and distinct variety of tangor tree, substantially as illustrated and described herein.

* * * * *